US008636799B2

(12) United States Patent
Sklar et al.

(10) Patent No.: US 8,636,799 B2
(45) Date of Patent: Jan. 28, 2014

(54) FIXATION SCREW, GRAFT LIGAMENT ANCHOR ASSEMBLY, AND METHOD FOR SECURING A GRAFT LIGAMENT IN A BONE TUNNEL

(76) Inventors: Joseph H. Sklar, Longmeadow, MA (US); Charles L. Beck, Jr., Salt Lake City, UT (US); Greta Jo Hays, North Logan, UT (US)

( * ) Notice: Subject to any disclaimer, the term of this patent is extended or adjusted under 35 U.S.C. 154(b) by 751 days.

(21) Appl. No.: 11/492,697

(22) Filed: Jul. 25, 2006

(65) Prior Publication Data

US 2007/0032870 A1    Feb. 8, 2007

Related U.S. Application Data

(63) Continuation of application No. 09/715,714, filed on Nov. 17, 2000, now Pat. No. 7,083,647, which is a continuation-in-part of application No. 09/248,523, filed on Feb. 9, 1999, now Pat. No. 6,533,816, and a continuation-in-part of application No. 09/304,885, filed on May 4, 1999, now abandoned, which is a continuation of application No. 08/756,413, filed on Nov. 27, 1996, now Pat. No. 5,899,938.

(51) Int. Cl.
  *A61F 2/08* (2006.01)
(52) U.S. Cl.
  USPC ...................................... 623/13.14
(58) Field of Classification Search
  USPC .................. 623/13.11–13.2; 606/72; 411/424
  See application file for complete search history.

(56) References Cited

U.S. PATENT DOCUMENTS

| RE13,204 E | 2/1911 | Jossart |
| 2,353,851 A | 7/1944 | Rosan |
| 3,153,975 A | 10/1964 | Rapata |
| 3,199,398 A | 8/1965 | Weisz |
| 3,411,397 A | 11/1968 | Birmingham |
| 3,516,324 A | 6/1970 | Berner |
| 3,678,798 A | 7/1972 | Van Niel |
| 3,731,724 A | 5/1973 | Dorflinger |
| 3,765,295 A | 10/1973 | Ptak |
| 3,832,931 A | 9/1974 | Talan |
| 3,942,407 A | 3/1976 | Mortensen |
| 3,976,079 A | 8/1976 | Samuels et al. |
| 4,083,289 A | 4/1978 | Erickson |

(Continued)

FOREIGN PATENT DOCUMENTS

| CA | 1015989 | 8/1977 |
| CA | 2272960 | 6/1998 |
| DE | 8914308.6 | 3/1990 |
| DE | 9109381 | 10/1991 |
| DE | 4127550 | 2/1993 |
| EP | 0358372 | 3/1990 |
| EP | 0425140 | 5/1991 |
| EP | 0596177 | 5/1994 |
| EP | 0596829 | 5/1994 |

(Continued)

OTHER PUBLICATIONS

Sklar, Joseph H., Intrafix[TM] Technique for Tibial Fixation of ACL Grafts, Innovasive Devices, a company brochure of Mitek Products, 1999.

*Primary Examiner* — Bruce E Snow
(74) *Attorney, Agent, or Firm* — Pandiscio & Pandiscio

(57) ABSTRACT

A fixation screw, graft ligament anchor assembly, and method for fastening a graft ligament in a bone tunnel. The screw comprises an elongated shank having a distal end and a proximal end, and a central axis extending from the distal end to the proximal end. Screw threads are disposed on the shank and extend from the distal end to the proximal end. The proximal end defines an end plane disposed transversely to the axis and at an angle thereto other than a normal angle.

4 Claims, 5 Drawing Sheets

(56) References Cited

U.S. PATENT DOCUMENTS

| | | | |
|---|---|---|---|
| 4,085,651 A | 4/1978 | Koscik | |
| 4,407,618 A | 10/1983 | Kimura | |
| 4,484,570 A | 11/1984 | Sutter et al. | |
| 4,535,925 A | 8/1985 | Ramey et al. | |
| 4,580,936 A | 4/1986 | Francis et al. | |
| 4,590,928 A | 5/1986 | Hunt et al. | |
| 4,708,132 A | 11/1987 | Silvestrini | |
| 4,708,397 A | 11/1987 | Weinmann | |
| 4,716,893 A | 1/1988 | Fischer et al. | |
| 4,744,793 A | 5/1988 | Parr et al. | |
| 4,755,183 A | 7/1988 | Kenna | |
| 4,778,468 A | 10/1988 | Hunt et al. | |
| 4,784,126 A | 11/1988 | Hourahane | |
| 4,828,562 A | 5/1989 | Kenna | |
| 4,851,005 A | 7/1989 | Hunt et al. | |
| 4,870,957 A | 10/1989 | Goble et al. | |
| 4,927,421 A | 5/1990 | Goble et al. | |
| 4,940,467 A | 7/1990 | Tronzo | |
| 4,944,742 A | 7/1990 | Clemow et al. | |
| 4,950,270 A | 8/1990 | Bowman et al. | |
| 4,950,271 A | 8/1990 | Lewis et al. | |
| 5,013,316 A | 5/1991 | Goble et al. | |
| 5,037,422 A | 8/1991 | Hayhurst et al. | |
| 5,062,843 A | 11/1991 | Mahony, III | |
| 5,108,431 A | 4/1992 | Mansat et al. | |
| 5,147,362 A | 9/1992 | Goble | |
| 5,151,104 A | 9/1992 | Kenna | |
| 5,152,790 A | 10/1992 | Rosenberg et al. | |
| 5,211,647 A | 5/1993 | Schmieding | |
| 5,234,430 A | 8/1993 | Huebner | |
| 5,236,445 A | 8/1993 | Hayhurst et al. | |
| 5,268,001 A | 12/1993 | Nicholson et al. | |
| 5,282,802 A | 2/1994 | Mahony, III | |
| 5,312,438 A | 5/1994 | Johnson | |
| 5,314,427 A | 5/1994 | Goble et al. | |
| 5,324,308 A | 6/1994 | Pierce | |
| 5,356,435 A | 10/1994 | Thein | |
| 5,360,448 A | 11/1994 | Thramann | |
| 5,360,450 A | 11/1994 | Giannini | |
| 5,376,119 A | 12/1994 | Zimmermann et al. | |
| 5,383,878 A | 1/1995 | Roger et al. | |
| 5,425,707 A | 6/1995 | Goldberg | |
| 5,425,767 A | 6/1995 | Steininger et al. | |
| 5,454,811 A | 10/1995 | Huebner | |
| 5,458,601 A | 10/1995 | Young, Jr. et al. | |
| 5,464,427 A | 11/1995 | Curtis et al. | |
| 5,470,334 A | 11/1995 | Ross et al. | |
| 5,480,403 A | 1/1996 | Lee et al. | |
| 5,486,197 A | 1/1996 | Le et al. | |
| 5,489,210 A | 2/1996 | Hanosh | |
| 5,562,669 A | 10/1996 | McGuire | |
| 5,584,835 A | 12/1996 | Greenfield | |
| 5,618,314 A | 4/1997 | Harwin et al. | |
| 5,632,748 A | 5/1997 | Beck, Jr. et al. | |
| 5,645,589 A | 7/1997 | Li | |
| 5,702,397 A | 12/1997 | Goble et al. | |
| 5,707,395 A | 1/1998 | Li | |
| 5,725,529 A | 3/1998 | Nicholson et al. | |
| 5,776,196 A | 7/1998 | Matsuzaki et al. | |
| 5,895,425 A | 4/1999 | Grafton et al. | |
| 5,899,938 A | 5/1999 | Sklar et al. | |
| 5,906,632 A | 5/1999 | Bolton | |
| 5,918,604 A | 7/1999 | Whelan | |
| 5,948,001 A | 9/1999 | Larsen | |
| 5,961,520 A | 10/1999 | Beck, Jr. et al. | |
| 5,989,253 A | 11/1999 | Bigliardi | |
| 6,099,530 A | 8/2000 | Simonian et al. | |
| 6,132,433 A | 10/2000 | Whelan | |
| 6,283,973 B1 * | 9/2001 | Hubbard et al. | 606/104 |
| 6,355,066 B1 | 3/2002 | Kim | |
| 6,371,124 B1 | 4/2002 | Whelan | |
| 6,379,361 B1 | 4/2002 | Beck, Jr. et al. | |
| 6,387,129 B2 * | 5/2002 | Rieser et al. | 623/13.14 |
| 6,517,579 B1 | 2/2003 | Paulos et al. | |
| 6,533,816 B2 * | 3/2003 | Sklar | 623/13.14 |
| 6,537,319 B2 | 3/2003 | Whelan | |
| 6,554,862 B2 | 4/2003 | Hays et al. | |
| 6,558,094 B2 | 5/2003 | Nehl | |
| 6,562,071 B2 | 5/2003 | Järvinen | |
| 6,575,987 B2 | 6/2003 | Gellman et al. | |
| 6,589,245 B1 * | 7/2003 | Weiler et al. | 623/13.14 |
| 6,616,694 B1 | 9/2003 | Hart | |
| 6,623,524 B2 | 9/2003 | Schmieding | |
| 6,632,245 B2 | 10/2003 | Kim | |
| 6,673,094 B1 | 1/2004 | McDevitt et al. | |
| 6,733,529 B2 | 5/2004 | Whelan | |
| 6,746,483 B1 | 6/2004 | Bojarski et al. | |
| 6,887,271 B2 | 5/2005 | Justin et al. | |
| 6,939,379 B2 | 9/2005 | Sklar | |
| 7,008,451 B2 | 3/2006 | Justin et al. | |
| 7,261,716 B2 | 8/2007 | Strobel et al. | |
| 7,309,355 B2 | 12/2007 | Donnelly et al. | |
| 7,329,281 B2 | 2/2008 | Hays et al. | |
| 2001/0007074 A1 | 7/2001 | Strobel et al. | |
| 2001/0047206 A1 | 11/2001 | Sklar et al. | |
| 2002/0007182 A1 | 1/2002 | Kim | |
| 2002/0040241 A1 | 4/2002 | Jarvinen | |
| 2002/0072797 A1 | 6/2002 | Hays et al. | |
| 2003/0065390 A1 | 4/2003 | Justin et al. | |
| 2003/0135274 A1 | 7/2003 | Hays et al. | |
| 2003/0144735 A1 | 7/2003 | Sklar et al. | |
| 2003/0191530 A1 | 10/2003 | Sklar | |
| 2004/0059415 A1 | 3/2004 | Schmieding | |
| 2004/0068262 A1 | 4/2004 | Lemos et al. | |
| 2004/0194789 A1 | 10/2004 | Whelan | |
| 2004/0267361 A1 | 12/2004 | Donnelly et al. | |
| 2005/0159748 A1 | 7/2005 | Clark | |
| 2005/0171603 A1 | 8/2005 | Justin et al. | |
| 2005/0216012 A1 | 9/2005 | Willmen | |
| 2006/0052787 A1 | 3/2006 | Re et al. | |
| 2006/0095130 A1 | 5/2006 | Caborn et al. | |
| 2006/0095131 A1 | 5/2006 | Justin et al. | |
| 2006/0100627 A1 | 5/2006 | Stone et al. | |
| 2006/0149258 A1 | 7/2006 | Sousa | |
| 2006/0189991 A1 | 8/2006 | Bickley | |
| 2007/0005069 A1 | 1/2007 | Contiliano et al. | |
| 2007/0023259 A1 | 2/2007 | Schonauer | |
| 2008/0015710 A1 | 1/2008 | Hays et al. | |
| 2008/0133007 A1 | 6/2008 | Donnelly et al. | |
| 2008/0154314 A1 | 6/2008 | McDevitt | |
| 2008/0161806 A1 | 7/2008 | Donnelly et al. | |
| 2008/0161864 A1 | 7/2008 | Beck et al. | |
| 2008/0228271 A1 | 9/2008 | Stone et al. | |

FOREIGN PATENT DOCUMENTS

| | | |
|---|---|---|
| EP | 0651979 | 5/1995 |
| EP | 0834281 | 4/1998 |
| EP | 0611557 | 8/1999 |
| EP | 1491162 | 12/2004 |
| FR | 2590792 | 6/1987 |
| FR | 2636835 | 3/1990 |
| FR | 2725615 | 4/1996 |
| JP | 05-300917 | 11/1993 |
| JP | 6086783 | 3/1994 |
| JP | 6-169944 | 6/1994 |
| JP | 8-066410 | 3/1996 |
| JP | H11511357 | 10/1999 |
| WO | WO-94/28799 | 12/1994 |
| WO | WO 98/22047 | 5/1998 |
| WO | WO-98/23229 | 6/1998 |
| WO | WO 99/52472 | 10/1999 |
| WO | WO 01/06909 | 2/2001 |
| WO | WO 01/30253 | 5/2001 |
| WO | WO 01/95835 | 12/2001 |
| WO | WO 02/32345 | 4/2002 |

* cited by examiner

FIXATION SCREW, GRAFT LIGAMENT ANCHOR ASSEMBLY, AND METHOD FOR SECURING A GRAFT LIGAMENT IN A BONE TUNNEL

REFERENCE TO PENDING PRIOR PATENT APPLICATIONS

This patent application is a continuation of prior U.S. patent application Ser. No. 09/715,714, filed Nov. 17, 2000 now U.S. Pat. No. 7,083,647 by Joseph H. Sklar et al. for FIXATION SCREW, GRAFT LIGAMENT ANCHOR ASSEMBLY, AND METHOD FOR SECURING A GRAFT LIGAMENT IN A BONE TUNNEL, which in turn is a continuation-in-part of (i) prior U.S. patent application Ser. No. 09/248,523, filed Feb. 9, 1999 now U.S. Pat. No. 6,533,816, by Joseph H. Sklar for GRAFT LIGAMENT ANCHOR AND METHOD FOR ATTACHING A GRAFT LIGAMENT TO A BONE; and (ii) prior U.S. patent application Ser. No. 09/304, 885, filed May 4, 1999 now abandoned by Joseph H. Sklar et al. for GRAFT LIGAMENT ANCHOR AND METHOD FOR ATTACHING A GRAFT LIGAMENT TO A BONE, which in turn is a continuation of prior U.S. patent application Ser. No. 08/756,413, filed Nov. 27, 1996 now U.S. Pat. No. 5,899,938 by Joseph H. Sklar et al. for GRAFT LIGAMENT ANCHOR AND METHOD FOR ATTACHING A GRAFT LIGAMENT TO A BONE.

FIELD OF THE INVENTION

This invention relates to medical apparatus and methods in general, and more particularly to apparatus and methods for reconstructing ligaments.

BACKGROUND OF THE INVENTION

Ligaments are tough bands of tissue which serve to connect the articular extremities of bones, or to support and/or retain organs in place within the body. Ligaments are typically composed of coarse bundles of dense white fibrous tissue which are disposed in a parallel or closely interlaced manner, with the fibrous tissue being pliant and flexible but not significantly extensible.

In many cases, ligaments are torn or ruptured as a result of accidents. Various procedures have been developed to repair or replace such damaged ligaments.

For example, in the human knee, the anterior and posterior cruciate ligaments (i.e., the "ACL" and "PCL") extend between the top end of the tibia and the bottom end of the femur. The ACL and PCL cooperate, together with other ligaments and soft tissue, to provide both static and dynamic stability to the knee. Often, the anterior cruciate ligament (i.e., the ACL) is ruptured or torn as a result of, for example, a sports-related injury. Consequently, various surgical procedures have been developed for reconstructing the ACL so as to restore substantially normal function to the knee.

In many instances, the ACL may be reconstructed by replacing the ruptured ACL with a graft ligament. More particularly, in such procedures, bone tunnels are generally formed in the top end of the tibia and the bottom end of the femur, with one end of the graft ligament being positioned in the femoral tunnel and the other end of the graft ligament being positioned in the tibial tunnel. The two ends of the graft ligament are anchored in place in various ways well known in the art so that the graft ligament extends between the bottom end of the femur and the top end of the tibia in substantially the same way, and with substantially the same function, as the original ACL. This graft ligament then cooperates with the surrounding anatomical structures so as to restore substantially normal function to the knee.

In some circumstances, the graft ligament may be a ligament or tendon which is harvested from elsewhere in the patient; in other circumstances, the graft ligament may be a synthetic device. For the purposes of the present invention, all of the foregoing are collectively referred to as a "graft ligament".

It has been found that in securing graft tendons to tibias, because of the surface configuration of the tibia bone it often is necessary to advance a fixation screw well into a bone tunnel in the tibia, often so far that for one side of the screw to be substantially flush with the bone tunnel opening, the other side of the screw will have advanced past the outer dense hard cortical bone and entered the inner and softer cancellous bone.

It has further been found that to refrain from advancing the fixation screw to the aforementioned location (that is, to leave a portion of the screw in cortical bone all around the screw) requires that a proximal portion of the screw remain outside the bone tunnel and project from the tibia.

Thus, there is a need for a fixation screw, graft ligament anchor assembly and method which affords full advancement of a fixation screw, but at the same time permits the screw to be engaged all around in the cortical portion of the tibia or other bone.

OBJECTS OF THE INVENTION

An object of the invention is to provide a fixation screw configured for disposition in cortical bone portions, so as to strengthen the retention of the screw in the bone.

Another object of the invention is to provide a fixation screw which, when the screw is fully implanted, substantially conforms to a surrounding bone surface at a proximal end of the screw.

A further object of the invention is to provide a graft ligament anchor assembly for improved retention in a bone, such as a tibia, and which in operative position conforms to a surrounding bone surface.

A still further object is to provide a method for securing a graft ligament in a bone tunnel so as to improve retention of the graft ligament in the bone, and so as to provide for conformance of a graft ligament anchor and fixation screw to a surface of surrounding bone.

SUMMARY OF THE INVENTION

With the above and other objects in view, as will hereinafter appear, there is provided a fixation screw for fastening a graft ligament in a bone tunnel. The screw comprises an elongated shank having a distal end and a proximal end, and a central axis extending from the distal end to the proximal end. Screw threads are disposed on the shank and extend from the distal end to the proximal end. The proximal end defines an end plane disposed transversely to the axis and at an angle thereto other than a normal angle.

In accordance with a further feature of the invention there is provided a fixation screw comprising an elongated shank having a generally conically-shaped distal end portion, a proximal end, and a central axis extending from the distal end portion to the proximal end. Screw threads are disposed on the shank and extend from the distal end portion to the proximal end. The proximal end comprises a generally planar end surface disposed transversely to the axis and at an angle thereto other than a normal angle.

In accordance with a further feature of the invention, there is provided a fixation screw for fastening a graft ligament in a bone tunnel. The screw comprises an elongated shank having a generally conically-shaped distal end portion, a proximal end, and a central axis extending from the distal end portion to the proximal end. Screw threads are disposed on the shank and extend from the distal end portion to the proximal end. The proximal end comprises a generally planar end surface disposed transversely to the axis and at an angle thereto other than a normal angle, and appropriate for positioning the end surface as generally a continuation of surrounding bone surface of a body in which the graft ligament is fastened.

In accordance with a further feature of the invention, there is provided a graft ligament anchor assembly comprising a tubular body having a bore therethrough, and proximal and distal ends. The tubular body is adapted for placement in a bone tunnel proximate an opening thereof in a bone surface. The tubular body comprises a deformable wall and defines, at least in part, a chamber for receiving a graft ligament therein. A fixation screw is provided for insertion into the tubular body axially of the tubular body, for impinging upon the deformable wall so as to press the deformable wall, and hence the graft ligament received in the chamber, toward a wall of the bore, to fix the graft ligament in the bone tunnel. The screw comprises an elongated shank having a generally conically-shaped distal end portion, a proximal end, and a central axis extending from the distal end portion to the proximal end. Screw threads are disposed on the shank and extend from the distal end portion to the proximal end. The proximal end comprises a generally planar end surface disposed transversely to the axis and at an angle thereto other than a normal angle, and appropriate for positioning as generally a continuation of surrounding bone surface of a body in which the graft ligament is fastened.

In accordance with a still further feature of the invention, there is provided a method for securing a graft ligament in a bone tunnel having an end opening in a bone surface, a free end of the graft ligament extending out of the bone tunnel end opening. The method comprises the steps of providing a fixation screw for insertion into the bone tunnel adjacent the graft ligament for impinging upon the graft ligament and a wall of the bone tunnel to fix the graft ligament in the bone tunnel. The screw comprises an elongated shank having a generally conically-shaped distal end portion, a proximal end, and a central axis extending from the distal end portion to the proximal end. Screw threads are disposed on the shank and extend from the distal end portion to the proximal end. The proximal end comprises a generally planar end surface disposed transversely to the axis and at an angle thereto other than a normal angle, and appropriate for positioning as generally a continuation of surrounding portions of the bone surface. The method further comprises the steps of pulling the graft ligament taut, inserting the screw into the bone tunnel and advancing the screw therein to threadedly engage the graft ligament and a wall of the bone tunnel to fix the graft ligament in the bone tunnel, and turning the screw until the shank proximal end surface thereof is substantially a continuation of the surrounding bone surface.

In accordance with another feature of the invention, there is provided a method for securing a graft ligament in a bone tunnel having an end opening in a bone surface, a free end of the graft ligament extending out of the bone tunnel end opening. The method comprises the step of providing a graft ligament anchor comprising a tubular body having a bore therethrough and proximal and distal ends, the tubular body comprising a deformable wall and defining at least in part a chamber, and a fixation screw. The screw comprises an elongated shank having a generally conically-shaped distal end portion, a proximal end, and a central axis extending from the distal end portion to the proximal end. Screw threads are disposed on the shank and extend from the distal end portion to the proximal end. The proximal end comprises a generally planar end surface disposed transversely to the axis and at an angle thereto other than a normal angle, and appropriate for positioning as generally a continuation of surrounding portions of the bone surface. The method includes the further steps of extending the graft ligament free end through the chamber, placing the tubular body in the end opening and in the bone tunnel, pulling the graft ligament taut, inserting the screw into the tubular body and advancing the screw therein to press the deformable wall, and hence the graft ligament received in the chamber, toward the wall of the bore, to fix the graft ligament in the bone tunnel, and turning the screw until the proximal end surface thereof is substantially a continuation of the bone surface therearound.

The above and other features of the invention, including various novel details of construction and combinations of parts and method steps will now be more particularly described with reference to the accompanying drawings and pointed out in the claims. It will be understood that the particular devices and method steps embodying the invention are shown by way of illustration only and not as limitations of the invention. The principles and features of this invention may be employed in various and numerous embodiments without departing from the scope of the invention.

BRIEF DESCRIPTION OF THE DRAWINGS

These and other objects and features of the present invention will be more fully disclosed or rendered obvious by the following detailed description of the preferred embodiments of the invention, which are to be considered together with the accompanying drawings wherein like numbers refer to like parts, and further wherein.

DETAILED DESCRIPTION OF THE PREFERRED EMBODIMENTS

Figure 1:
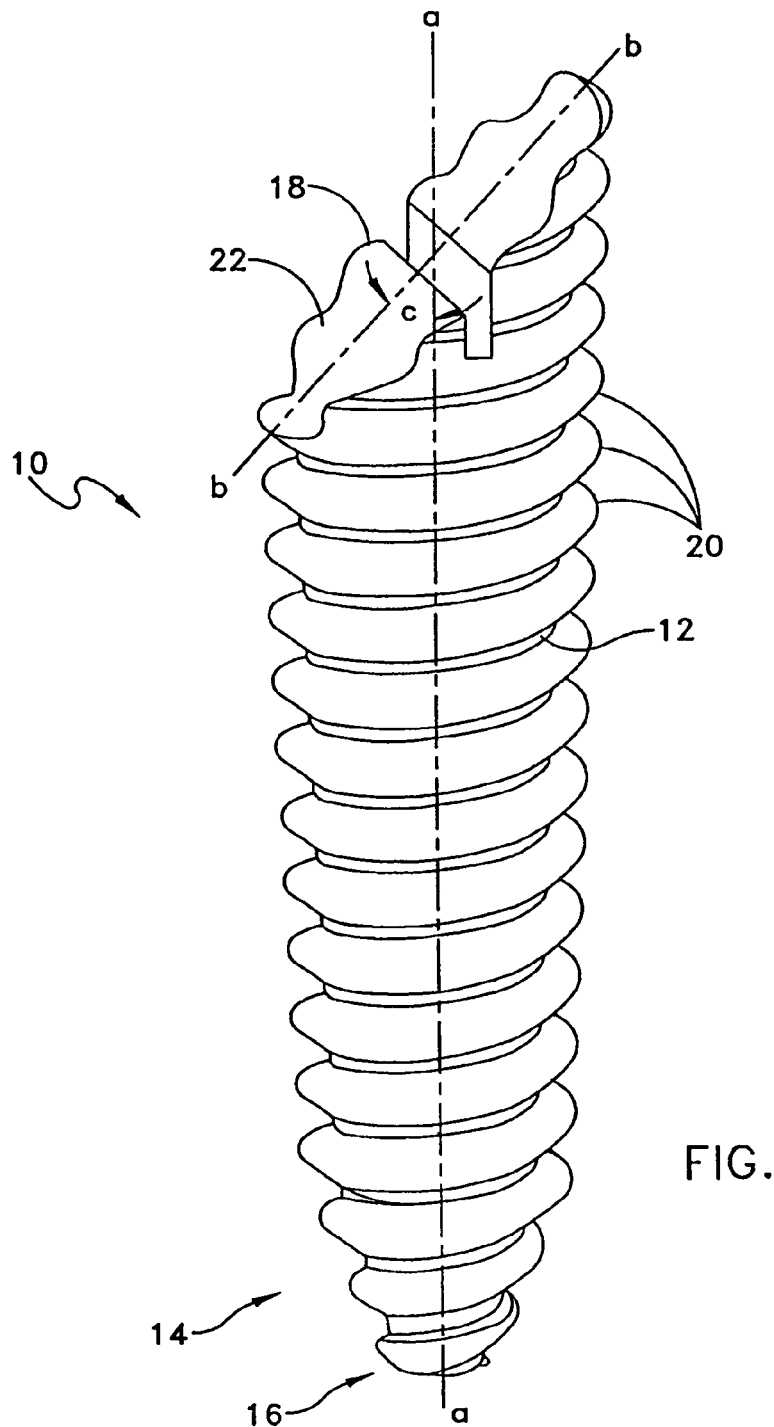
FIG. 1 is a perspective view of one form of a fixation screw for fastening a graft ligament in a bone tunnel, illustrative of an embodiment of the invention.

Referring to FIG. 1, it will be seen that an illustrative fixation screw 10 includes an elongated shank 12 having a distal end portion 14, which may be generally conically-shaped, as shown in FIG. 1, and have a generally pointed distal end 16. The shank 12 is further provided with a proximal end 18 defining an end plane b-b. A central axis a-a extends from the distal end 16 to the proximal end 18. The plane b-b is disposed transversely to the axis a-a and at an angle c thereto, the angle c being other than a normal angle, and preferably of about 40°-55°. The proximal end 18 may comprise a generally planar surface 22, as illustrated in FIG. 1. Screw threads 20 are disposed on the shank 12 and extend from the distal end 16 to the proximal end 18.

Figure 2:
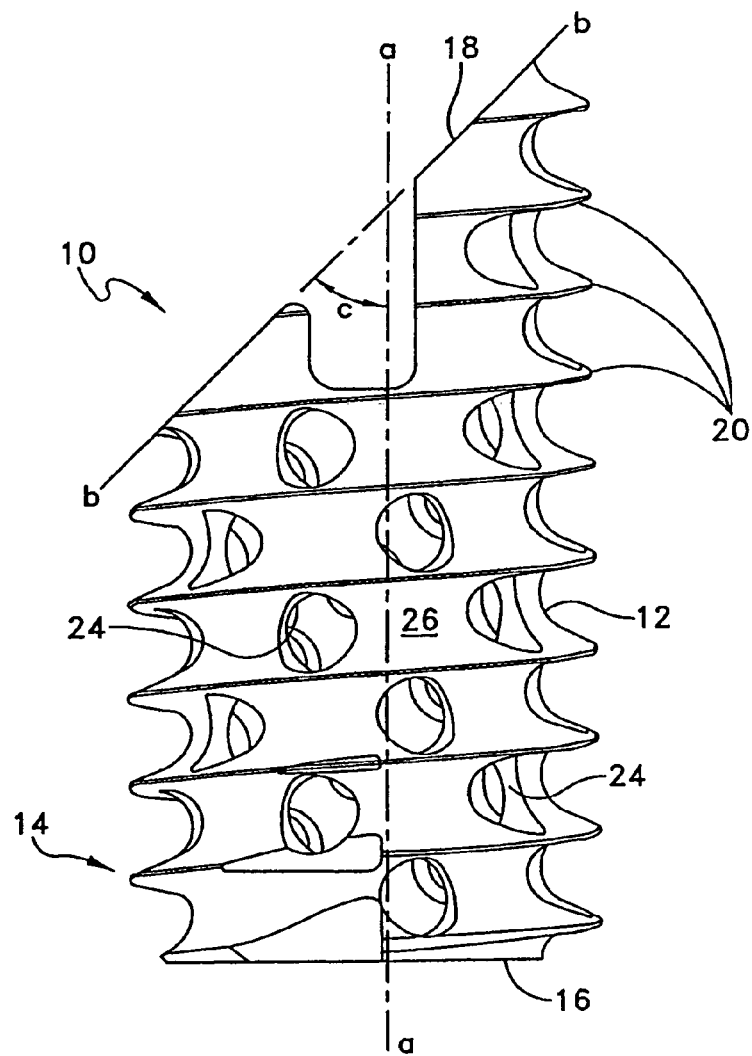
FIG. 2 is a side elevational view of an alternative embodiment of fixation screw.

Referring to FIG. 2, it will be seen that the fixation screw 10 may be of tubular structure and provided with apertures 24 extending through sidewalls 26 thereof, facilitating in-growth of bone to further secure the screw in place over time. Further, as shown in FIG. 2, the distal end portion 14 of the screw 10 may be other than conical, such as generally cylindrical, and the distal end 16 of the screw 10 may be other than pointed, such as defining a plane normal to the axis a-a.

Figure 3:
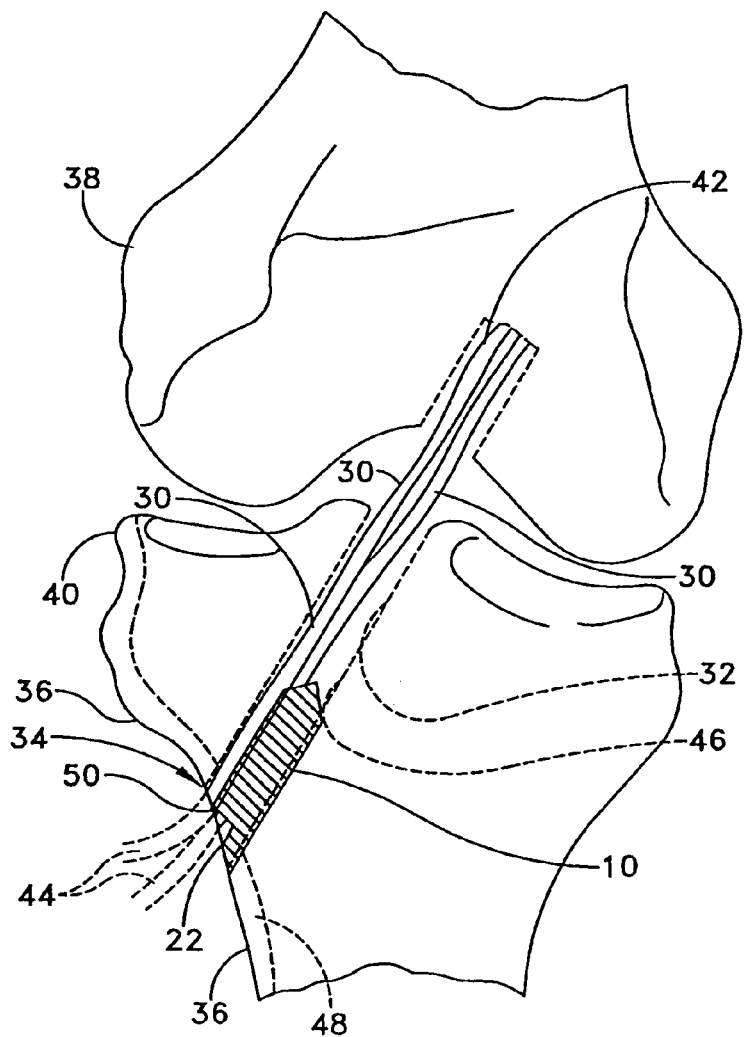
FIG. 3 is a diagrammatic illustration of the screw of FIG. 1 in operation.

In FIG. 3, there is illustrated a manner in which the fixation screw 10 of FIG. 1 or FIG. 2 may be used to secure a graft ligament 30 in a bone tunnel 32 having an end opening 34 in a bone surface 36. In FIG. 3, the bones shown for illustrative purposes are major bones of a knee joint, including a femur 38 and tibia 40. The invention presumes that one end 42 of the ligament 30 has been secured in the femur in accordance with known methods and that another end portion 44 extends from the end opening 34.

In the method illustrated in FIG. 3, an operator pulls the ligament 30 taut by manipulation of the exposed ligament end portion 44. The screw 10 is then inserted into the bone tunnel 32, by way of the end opening 34. The screw 10 is advanced into the bone tunnel 32, threadedly engaging the ligament 30 and a wall 46 of the bone tunnel 32, to secure the ligament 30 in the bone tunnel 32. As the screw 10 advances to nearly full insertion, the screw is turned until the shank proximal end surface 22 is disposed so as to be substantially flush with, and form substantially a continuation of, the surrounding bone surface 36.

Thus, threaded portions of the screw 10 are engaged throughout 360° with cortical portions 48 of the tibia 40, or other selected bone, to securely retain the screw in place. With the screw 10 in place, the exposed ligament end portions 44 may be snipped off along lines 50, shown in FIG. 3 (the "snipped off" portions of ligament end portions 44 are shown in phantom in FIG. 3). As noted above, when the embodiment of fixation screw shown in FIG. 2 is used, over time material from the bone wall 46 will migrate through the apertures 24, to further lock the screw in place.

Figure 4:
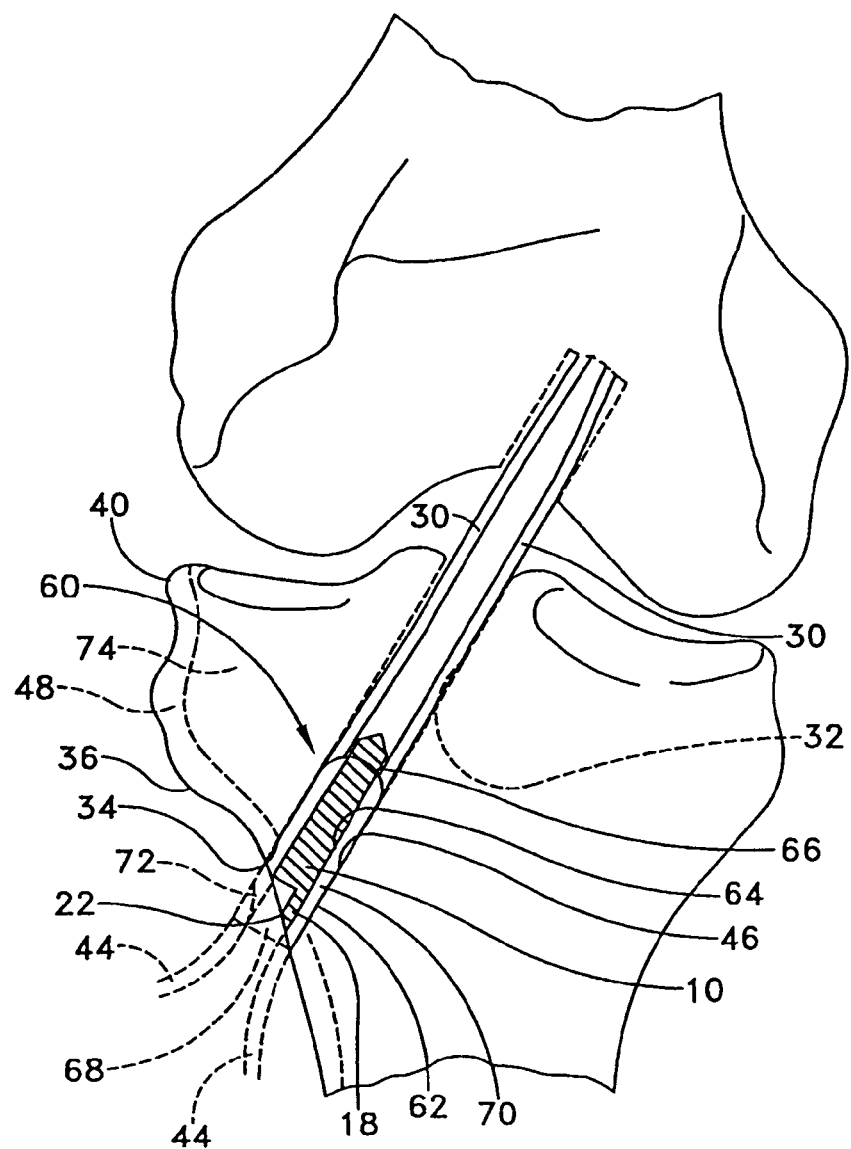
FIG. 4 is a diagrammatic illustration of a graft ligament anchor assembly including the screw of FIG. 1 and illustrating an anchor assembly in operation.

In FIG. 4, there is shown a graft ligament anchor 60 in a tibia 40. The anchor 60 includes the screw 10, as described hereinabove, and a tubular body 62 having a bore 64 therethrough and having distal and proximal ends 66, 68. The tubular body 62 is adapted for placement in the bone tunnel 32 proximate the end opening 34 thereof in the bone surface 36. A deformable wall 70 is disposed in the tubular body, defining at least in part a chamber 72 for receiving the graft ligament 30 therein.

In the anchor assembly 60 shown in FIG. 4, the tubular body 62 itself forms a deformable wall 70. In pending prior U.S. patent application Ser. No. 09/248,523, filed Feb. 9, 1999 by Joseph H. Sklar for GRAFT LIGAMENT ANCHOR AND METHOD FOR ATTACHING A GRAFT LIGAMENT TO A BONE, which pending prior patent application is hereby incorporated herein by reference, there are disclosed several ligament anchor assemblies having tubular bodies with alternative arrangements of deformable walls and appropriate for use in the anchor assembly presented herein.

In use of the graft ligament anchor assembly, the ligament end portions 44 are extended through the tubular body chamber 72 by an operator. The tubular body 62 is inserted in the end opening 34 of the bone tunnel 32. The ligament 30 is pulled taut by the operator. The fixation screw 10 is then inserted into the tubular body 62 and advanced to press the graft ligament 30 and deformable wall 70 toward the wall 46 of the bone tunnel 32, to fix the ligament to the bone tunnel wall 46. As the proximal end 18 of the screw 10 draws near the bone surface 36, the screw 10 is turned until the screw proximal end surface 22 is disposed so as to be flush with, and substantially a continuation of, the bone surface 36 therearound.

The tubular body 62 and the ligament end portions 44 may then be snipped off to provide a relatively smooth surface in the area of the closed opening 34 (the "snipped off" portions of tubular body 62 and the ligament end portions 44 are shown in phantom in FIG. 4).

In the embodiment shown in FIG. 4, the threads 20 of the screw 10 do not directly engage the cortical bone 48; however, the threads 20 force the tubular body 62 into engagement with the cortical bone 48, providing stronger fixation than if similarly engaged with a cancellous portion 74 of the bone 40.

There is thus provided an improved fixation screw, graft ligament anchor assembly and methods for fixing ligaments in bone tunnels.

In the aforementioned U.S. patent application Ser. No. 09/248,523, which patent application has already been incorporated herein by reference, there are also disclosed bone tunnel liners for lining the wall of a bone tunnel prior to securing a graft ligament therein.

Figure 5:
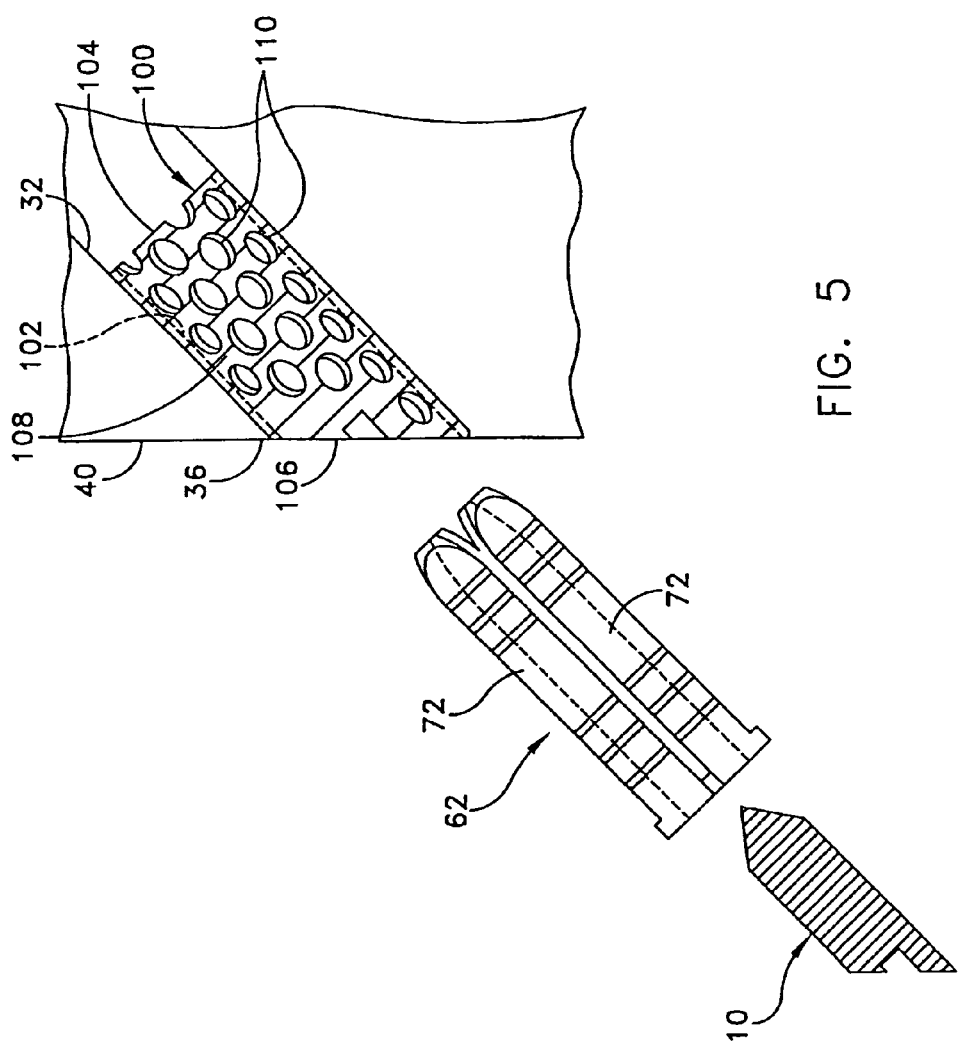
FIG. 5 is a diagrammatic illustration of still another embodiment of the present invention.

Looking now at FIG. 5, there is shown a bone tunnel liner 100 which may be positioned within a bone tunnel 32 of a bone 40. Bone tunnel liner 100 includes a central bore 102 extending from its distal end 104 to its proximal end 106. The outer surface of bone tunnel liner 100 includes screw threads 108 and preferably includes openings 110. In use, bone tunnel liner 100 is positioned in bone tunnel 32 in bone 40, the graft ligament's end portions are extended through chambers 72 of tubular body 62, tubular body 62 is inserted into bone tunnel liner 100, and fixation screw 10 is inserted into the central bore of tubular body 62 and advanced distally so as to press the tubular body's deformable walls, and hence the graft ligament, toward bone tunnel liner 100, whereby to secure the graft ligament in the bone tunnel.

In accordance with the present invention, the proximal end 106 of bone tunnel liner 100 is preferably formed with an end surface which is set at an angle to the longitudinal axis of the bone tunnel liner, whereby the proximal end of the bone tunnel liner may be disposed flush with, and substantially a continuation of, the bone surface 36 therearound.

It is to be understood that the present invention is by no means limited to the particular construction and method steps herein disclosed and/or shown in the drawings, but also comprises any modification or equivalent within the scope of the claims. For example, it will be apparent that the particular inclination of the proximal end plane to the shank central axis is selected to match the bone surface 36. The angle is determined by the application site morphology.

What is claimed is:

1. A method for securing a graft ligament in a bone tunnel having an end opening in a bone surface, a free end of the graft ligament extending out of the bone tunnel end opening, the method comprising the steps of:

providing a tubular fixation screw for insertion into the bone tunnel adjacent the graft ligament for impinging upon the graft ligament and a wall of the bone tunnel to fix the graft ligament to the wall in the bone tunnel, the screw comprising:

an elongated tubular shank provided with apertures extending through sidewalls thereof, and having a proximal end extending along a plane at a non-right angle to a center axis of the shank;

a generally planar distal end extending along a plane normal to the center axis of the shank;

the center axis extending from the distal end to the proximal end; and screw threads disposed on the tubular shank and extending from the distal end to the proximal end;

wherein the apertures in the shank are disposed between the screw threads, and wherein a plurality of the apertures are disposed in straight rows extending lengthwise of the tubular shank, each lengthwise row of apertures comprising apertures in each of said lengthwise rows separated from each other by a widthwise extending screw thread devoid of an aperture in the lengthwise row; and said plurality of apertures are disposed in widthwise grooves between the screw threads;

the lengthwise rows of apertures being spaced from each other widthwise of the shank, such that each aperture is spaced widthwise from a neighboring aperture by a wall portion of the shank and each aperture is disposed in the lengthwise row of apertures;

whereby each of the apertures is adjacent sidewall portions and spaced from other apertures by the sidewall portions;

the proximal end comprising a slanted end surface disposed transversely to the central axis and at an angle thereto other than a normal angle, and appropriate for positioning as generally a continuation of surrounding portions of the bone surface;

pulling the graft ligament taut;

inserting the fixation screw into the bone tunnel and advancing the screw therein to threadedly engage the graft ligament and the wall of the bone tunnel to fix the graft ligament in the bone tunnel; and turning the screw until the shank proximal end surface thereof is substantially flush with the surrounding bone surface, and the apertures extending through the shank sidewalls are disposed to receive migration of material from the bone tunnel wall to lock the screw and the graft ligament in the bone tunnel.

2. The method in accordance with claim 1 wherein the proximal end plane extends through a plurality of said screw threads.

3. The method in accordance with claim 1 and comprising a further step of snipping off exposed portions of the graft ligament.

4. The method in accordance with claim 1 wherein the turning of the screw engages the screw threads and the apertures with the material of the bone wall.

* * * * *